(12) United States Patent
Harms

(10) Patent No.: US 9,687,614 B2
(45) Date of Patent: Jun. 27, 2017

(54) ASSEMBLY FOR A DRUG DELIVERY DEVICE

(71) Applicant: Michael Harms, Frankfurt am Main (DE)

(72) Inventor: Michael Harms, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 413 days.

(21) Appl. No.: 14/350,573

(22) PCT Filed: Oct. 11, 2012

(86) PCT No.: PCT/EP2012/070099
§ 371 (c)(1),
(2) Date: Apr. 9, 2014

(87) PCT Pub. No.: WO2013/053781
PCT Pub. Date: Apr. 18, 2013

(65) Prior Publication Data
US 2014/0288505 A1    Sep. 25, 2014

(30) Foreign Application Priority Data
Oct. 14, 2011   (EP) .................................... 11185135

(51) Int. Cl.
*A61M 5/00*        (2006.01)
*A61M 5/315*       (2006.01)

(52) U.S. Cl.
CPC .... *A61M 5/31585* (2013.01); *A61M 5/31501* (2013.01); *A61M 5/31543* (2013.01); *A61M 5/31595* (2013.01)

(58) Field of Classification Search
CPC .......... A61M 5/31585; A61M 5/31595; A61M 5/31501; A61M 5/31543; A61M 5/315

(Continued)

(56) References Cited

U.S. PATENT DOCUMENTS

| 4,865,591 A * | 9/1989 | Sams ................ A61M 5/31553 |
| | | 222/287 |
| 4,936,833 A | 6/1990 | Sams |
| 8,568,141 B2 | 10/2013 | Tanaka et al. |

FOREIGN PATENT DOCUMENTS

| EP | 0295075 A1 | 12/1988 |
| EP | 1923083 A1 | 5/2008 |

(Continued)

OTHER PUBLICATIONS

English Translation of Notice of Reasons for Rejection issued in Japanese Patent Application No. 2014-535059 dated Sep. 2, 2016.

*Primary Examiner* — Bhisma Mehta
*Assistant Examiner* — Hamza Darb
(74) *Attorney, Agent, or Firm* — McDonnell Boehnen Hulbert & Berghoff LLP

(57) ABSTRACT

An assembly for a drug delivery device is provided the assembly comprising a cartridge adapted and arranged to contain at least one dose of a drug, a bung being slidably arranged within the cartridge, a housing comprising a distal end and a proximal end, and a piston rod adapted and arranged for moving the bung in the distal direction with respect to the housing for dispensing a dose of the drug. The assembly further comprises a drive member and arranged for transferring movement to the piston rod for dispensing the dose, and an engagement member configured to mechanically cooperate with the piston rod and with the housing. The engagement member is moveable between a reset position, where the engagement member is allowed to rotate with respect to the housing, and an operating position, where the engagement member is rotationally locked with respect to the housing, wherein the assembly is configured such that the engagement member is rotated and simultaneously axially displaced during movement of the engagement member between the operating position and the reset position. The (Continued)

engagement member and the housing are threadedly engaged with one another, wherein at least one of the engagement member and the housing comprises a thread and the other one of the engagement member and the housing comprises an interaction. Furthermore, the use of an engagement member for a drug delivery device is described.

10 Claims, 4 Drawing Sheets

(58) Field of Classification Search
USPC .................................................. 604/207–212
See application file for complete search history.

(56) References Cited

FOREIGN PATENT DOCUMENTS

| | | | |
|---|---|---|---|
| JP | 63318952 | A | 12/1988 |
| WO | 2009132777 | A1 | 11/2009 |
| WO | 2010150396 | A1 | 12/2010 |
| WO | 2011039203 | A2 | 4/2011 |
| WO | 2011039216 | A2 | 4/2011 |
| WO | 2011101383 | A1 | 8/2011 |

* cited by examiner

ASSEMBLY FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2012/070099 filed Oct. 11, 2012, which claims priority to European Patent Application No. 11185135.8 filed Oct. 14, 2011. The entire disclosure contents of these applications are herewith incorporated by reference into the present application.

FIELD OF INVENTION

This disclosure relates to an assembly for a drug delivery device.

BACKGROUND

In a drug delivery device, often, a bung within a cartridge containing a plurality of doses of a drug is displaced by a piston rod. Thereby, a dose of the drug is expelled from the cartridge.

A drug delivery device is described in document EP 1 923 083 A1, for example.

SUMMARY

It is an object of the present disclosure to provide an improved drug delivery device, for example a device with increased user comfort and/or a cost-effective drug delivery device.

This object may be achieved by the subject matter of the independent claims. Advantageous embodiments and refinements are subject matter of the dependent claims.

One aspect relates to an assembly for a drug delivery device. The assembly may comprise a cartridge. The cartridge may be adapted and arranged to contain at least one dose of a drug, preferably a plurality of doses of the drug. A bung may be slidably arranged within the cartridge. The assembly may comprise a housing. The housing may comprise a distal end and a proximal end. The assembly may further comprise a piston rod. The piston rod may be adapted and arranged for moving the bung in the distal direction with respect to the housing for dispensing a dose of the drug. The assembly may further comprise a drive member. The drive member may be adapted and arranged for transferring movement to the piston rod for dispensing the dose. The assembly may further comprise an engagement member. The engagement member may be configured to mechanically cooperate with the piston rod and with the housing. The engagement member may be moveable between a reset position and an operating position. In the reset position, the engagement member may be allowed to rotate with respect to the housing. In the operating position, the engagement member may be rotationally locked with respect to the housing. The assembly may be configured such that the engagement member is rotated and simultaneously axially displaced during movement of the engagement member between the operating position and the reset position. The engagement member and the housing may be threadedly engaged with one another. At least one of the engagement member and the housing may comprise a thread and the other one of the engagement member and the housing may comprise an interaction element engaging the thread to establish the threaded engagement. Alternatively, the thread or the interaction element may be provided on a member, e.g. an insert, which is fixedly attached to the housing, in particular secured against axial and rotational movement with respect to the housing.

The term "threadedly engaged" shall preferably mean the interlocking of helical threads of the components, e.g. the housing and the engagement member. Alternatively, the term "threadedly engaged" may mean the interlocking of a helical thread of one component, e.g. the housing, and parts of a thread of the other component, e.g. the engagement member. Alternatively, the term "threadedly engaged" may mean the interlocking of a helical thread of one component, e.g. the housing, and at least one projection of the other component, e.g. the engagement member.

Accordingly, the interaction element may comprise at least one of a thread, a part of a thread and a knob. The interaction element may be provided on the engagement member, in particular on an outer surface of the engagement member.

Due to the threaded engagement of the housing and the engagement member, the engagement member may be easily moveable, in particular axially and rotationally displaceable, from the operating position to the reset position and vice versa. In this way, performance of an easy and quick reset operation of the device for dispensing a plurality of doses from a replacement cartridge is enabled. The easily performable reset of the device may help to increase user comfort of the device. Furthermore, by enabling the reset operation, the lifetime of the device may be increased as the device can be used with a plurality of replacement cartridges. Hence, a very cost-effective device is provided which can be used multiple times.

Furthermore, the engagement member and the piston rod may be threadedly engaged with one another. For this purpose, at least one of the engagement member and the piston rod may comprise a further thread and the other one of the engagement member and the piston rod may comprise a further interaction element engaging the further thread to establish the threaded engagement.

The further interaction element may be provided on the engagement member, in particular on an inner surface of the engagement member, for example. The further interaction element and the further thread are configured to mechanically cooperate with one another such that the engagement member and the piston rod are threadedly engaged for axially and simultaneously moving the engagement member between the reset position and the operating position.

Preferably, the thread provided by at least one of the housing and the engagement member comprises an equal lead as compared to the further thread provided by at least one of the engagement member and the piston rod. Preferably, the thread provided by at least one of the housing and the engagement member comprises an equal pitch as compared to the further thread provided by at least one of the engagement member and the piston rod. Preferably, the thread provided by at least one of the housing and the engagement member is equally handed as compared to the further thread provided by at least one of the engagement member and the piston rod. In this way, the engagement member may be rotatable with respect to the piston rod and with respect to the housing when being moved between the reset position and the operating position. If the thread provided by at least one of the housing and the engagement member would not comprise an equal lead and/or hand as compared to the further thread provided by at least one of the engagement member and the piston rod, movement of the engagement member between the operating position and the reset position would be impossible.

The term "pitch" shall preferably mean the distance between consecutive contours on a helical thread, measured parallel to the axis of the helical thread.

The term "lead" shall preferably mean the axial distance a nut would advance in one complete revolution. Preferably, "lead" shall mean the axial distance through which a component having a helical thread, e.g. the piston rod, may travel during one rotation. Therefore, lead is a function of the pitch of the thread of the relevant component.

A further aspect relates to the use of an engagement member for a drug delivery device. An inner surface of the engagement member may be provided with an interaction element. Furthermore, an outer surface of the interaction member may be provided with a further interaction element. The interaction elements may be provided to threadedly engage with two different threads of equal pitch and hands. The engagement member may be used for simultaneously establishing the threaded engagement with the two different threads.

One of the two different threads may be provided on a housing of the device, for example. The other of the two different threads may be provided on a piston rod of the device, for example. The two threads may be equally handed.

Mechanical cooperation of the respective interaction element with the respective thread allows a combined axial and rotational movement of the engagement member with respect to the two components the two different threads are provided on, e.g. the housing and the piston rod of the drug delivery device. Accordingly, the engagement member can be rotationally and axially displaced with respect to the two components, e.g. for resetting the device. This may help to increase user comfort of the device. Furthermore, by enabling such a reset operation, the lifetime of the device may be increased. Hence, a cost-effective drug delivery device may be provided.

Of course, features described above in connection with different aspects and embodiments may be combined with each other and with features described below.

BRIEF DESCRIPTION OF THE DRAWINGS

Further features and refinements become apparent from the following description of the exemplary embodiments in connection with the accompanying figures.

Like elements, elements of the same kind and identically acting elements may be provided with the same reference numerals in the figures.

DETAILED DESCRIPTION

Figure 1A:
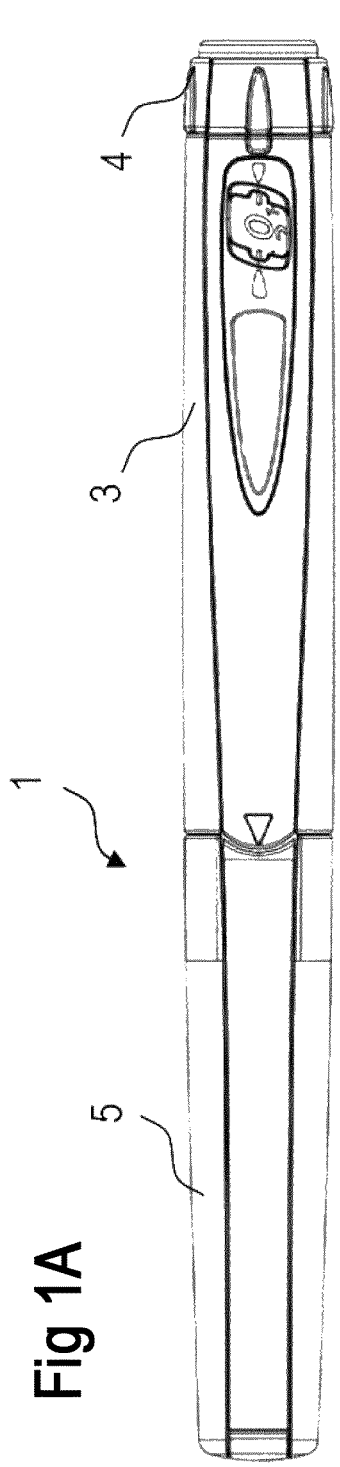
FIGS. 1A and 1B schematically show a perspective side view of a drug delivery device, FIG. 2 schematically shows a sectional side view of the drug delivery device of FIGS. 1A and 1B, FIG. 3 schematically shows a perspective side view of parts of the drug delivery device of FIG. 2, FIG. 4 schematically shows a sectional side view of parts of the drug delivery device of FIG. 2.
Figure 1B:
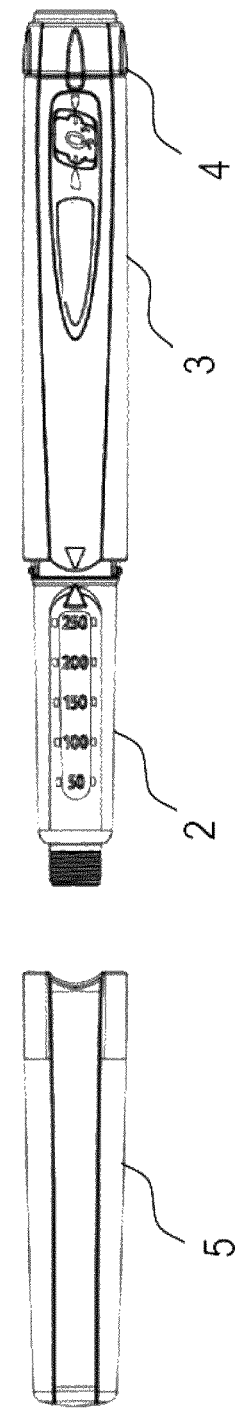
Figure 2:
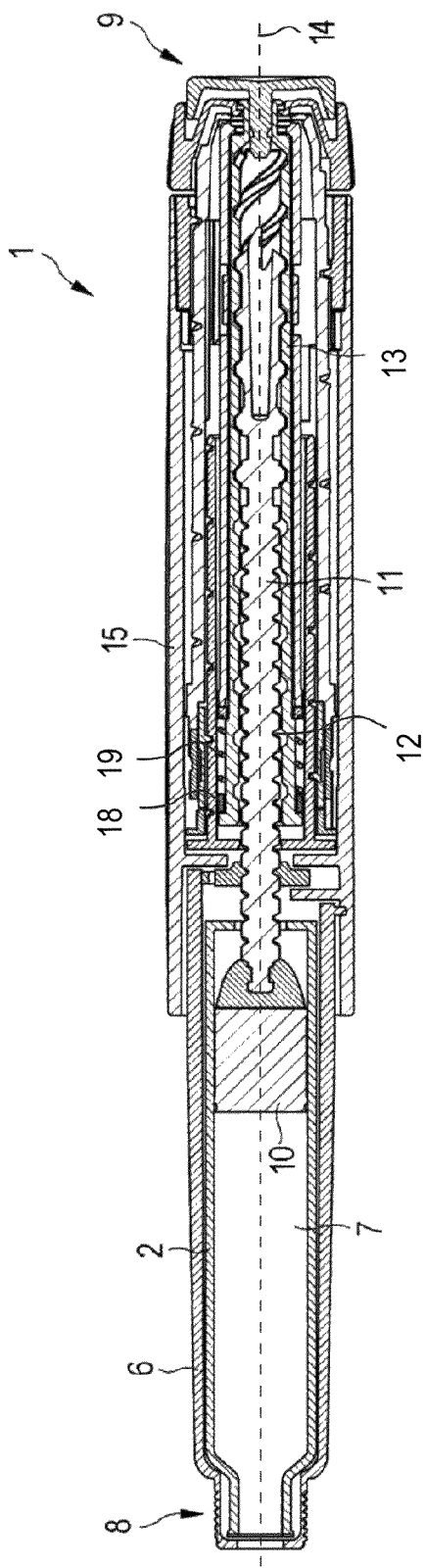

In FIGS. 1A, 1B and 2 a drug delivery device 1 is shown. The drug delivery device 1 comprises a housing 3. The drug delivery device 1 and the housing 3 have a distal end and a proximal end. The distal end is indicated by arrow 8 (see FIG. 2). The proximal end is indicated by arrow 9 (see FIG. 2). The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis 14 of the device 1 (see FIG. 2).

The drug delivery device 1 comprises a cartridge holder 6 (FIG. 2). The drug delivery device 1 comprises a cartridge 2. The cartridge 2 is retained within the cartridge holder 6. The cartridge holder 6 stabilizes the position of the cartridge 2 mechanically. The cartridge holder 6 is releasably connectable, e.g. by a threaded engagement, to the housing 3. Alternatively, the cartridge 2 may be releasably connected to the housing 3. In this case, the cartridge holder 6 may be redundant (see FIGS. 1A and 1B). A cap 5 (see FIGS. 1A and 1B) can be secured to the drug delivery device 1 for protecting the device 1, and, in particular, the cartridge holder 6 or the cartridge 2 from environmental influences.

The cartridge 2 contains a drug 7, preferably a plurality of doses of the drug 7. The term "drug", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω- carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:

```
H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28]Exendin-4(1-39), des Pro36 [IsoAsp28]Exendin-4(1-39), des Pro36 [Met(O)14, Asp28]Exendin-4(1-39), des Pro36 [Met(O)14, IsoAsp28]Exendin-4(1-39), des Pro36 [Trp(O2)25, Asp28]Exendin-4(1-39), des Pro36 [Trp(O2)25, IsoAsp28]Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39);
or des Pro36 [Asp28]Exendin-4(1-39), des Pro36 [IsoAsp28]Exendin-4(1-39), des Pro36 [Met(O)14, Asp28]Exendin-4(1-39), des Pro36 [Met(O)14, IsoAsp28]Exendin-4(1-39), des Pro36 [Trp(O2)25, Asp28]Exendin-4(1-39), des Pro36 [Trp(O2)25, IsoAsp28]Exendin-4(1-39), des Pro36 [Met(O)14 Trp(O2)25, Asp28]Exendin-
4(1-39), des Pro36 [Met(O)14 Trp(O2)25, IsoAsp28]
Exendin-4(1-39),
``` wherein the group -Lys6-NH2 may be bound to the C-terminus of the Exendin-4 derivative;

```
or an Exendin-4 derivative of the sequence des Pro36 Exendin-4(1-39)-Lys6-NH2 (AVE0010), H-(Lys)6-des Pro36 [Asp28]Exendin-4(1-39)-Lys6-NH2, des Asp28 Pro36, Pro37, Pro38Exendin-4(1-39)-NH2, H-(Lys)6-des Pro36, Pro38 [Asp28]Exendin-4(1-39)-
NH2, H-Asn-(Glu)5des Pro36, Pro37, Pro38 [Asp28]Exendin-
4(1-39)-NH2, des Pro36, Pro37, Pro38 [Asp28]Exendin-4(1-39)-
(Lys)6-NH2, H-(Lys)6-des Pro36, Pro37, Pro38 [Asp28]Exendin-
4(1-39)-(Lys)6-NH2, H-Asn-(Glu)5-des Pro36, Pro37, Pro38 [Asp28]
Exendin-4(1-39)-(Lys)6-NH2, H-(Lys)6-des Pro36 [Trp(O2)25, Asp28]Exendin-4
(1-39)-Lys6-NH2, H-des Asp28 Pro36, Pro37, Pro38 [Trp(O2)25]
Exendin-4(1-39)-NH2, H-(Lys)6-des Pro36, Pro37, Pro38 [Trp(O2)25, Asp28]
Exendin-4(1-39)-NH2, H-Asn-(Glu)5-des Pro36, Pro37, Pro38 [Trp(O2)25,
Asp28]Exendin-4(1-39)-NH2, es Pro36, Pro37, Pro38 [Trp(O2)25, Asp28]
Exendin-4(1-39)-(Lys)6-NH2, H-(Lys)6-des Pro36, Pro37, Pro38 [Trp(O2)25, Asp28]
Exendin-4(1-39)-(Lys)6-NH2, H-Asn-(Glu)5-des Pro36, Pro37, Pro38 [Trp(O2)25,
Asp28]Exendin-4(1-39)-(Lys)6-NH2, H-(Lys)6-des Pro36 [Met(O)14, Asp28]
Exendin-4(1-39)-Lys6-NH2, des Met(O)14 Asp28 Pro36, Pro37, Pro38 Exendin-
4(1-39)-NH2, H-(Lys)6-desPro36, Pro37, Pro38 [Met(O)14, Asp28]
Exendin-4(1-39)-NH2, H-Asn-(Glu)5-des Pro36, Pro37, Pro38 [Met(O)14,
Asp28]Exendin-4(1-39)-NH2, des Pro36, Pro37, Pro38 [Met(O)14, Asp28]
Exendin-4(1-39)-(Lys)6-NH2, H-(Lys)6-des Pro36, Pro37, Pro38 [Met(O)14, Asp28]
Exendin-4(1-39)-(Lys)6-NH2, H-Asn-(Glu)5 des Pro36, Pro37, Pro38 [Met(O)14,
Asp28]Exendin-4(1-39)-(Lys)6-NH2, H-Lys6-des Pro36 [Met(O)14, Trp(O2)25, Asp28]
Exendin-4(1-39)-Lys6-NH2, H-des Asp28 Pro36, Pro37, Pro38 [Met(O)14,
Trp(O2)25]Exendin-4(1-39)-NH2, H-(Lys)6-des Pro36, Pro37, Pro38 [Met(O)14, Asp28]
Exendin-4(1-39)-NH2, H-Asn-(Glu)5-des Pro36, Pro37, Pro38 [Met(O)14,
Trp(O2)25, Asp28]Exendin-4(1-39)-NH2, des Pro36, Pro37, Pro38 [Met(O)14, Trp(O2)25,
Asp28]Exendin-4(1-39)-(Lys)6-NH2, H-(Lys)6-des Pro36, Pro37, Pro38 [Met(O)14,
Trp(O2)25,Asp28]Exendin-4(S1-39)-(Lys)6-NH2, H-Asn-(Glu)5-des Pro36, Pro37, Pro38 [Met(O)14,
Trp(O2)25, Asp28]Exendin-4(1-39)-(Lys)6-NH2;
``` or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A bung 10 is slideably retained within the cartridge 2. The bung 10 seals the cartridge 2 proximally. Movement of the bung 10 in the distal direction with respect to the cartridge 2 causes the drug 7 to be dispensed from the cartridge 2. A detailed description of the operation and the functionality of the device 1 shown in FIG. 2 is given in document WO 2009/132777 A1 which is herewith incorporated by reference.

Figure 3:
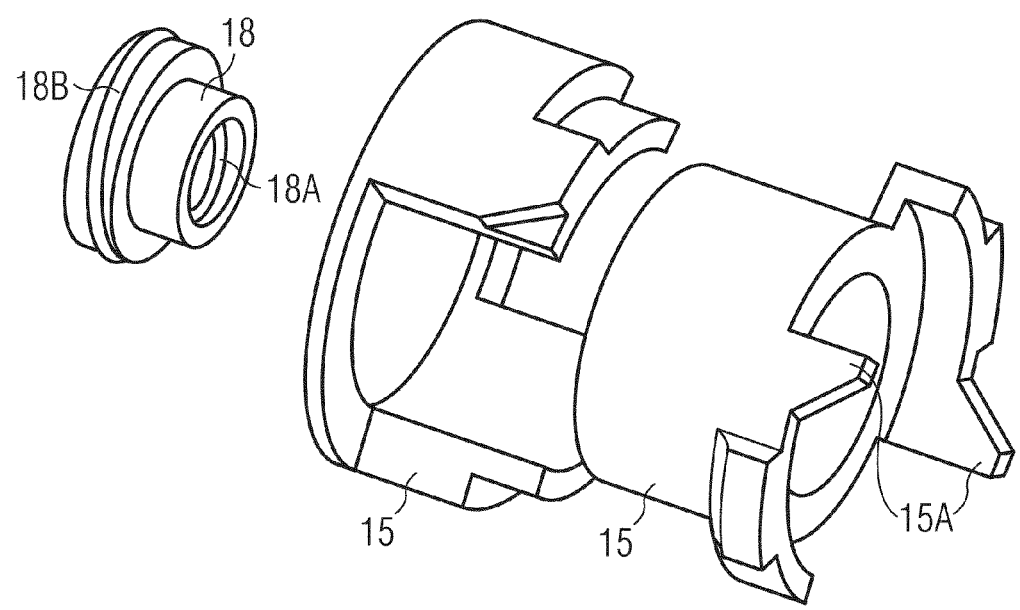

The device 1 comprises a dosing assembly 15 (see also FIG. 3). The dosing assembly 15 is arranged at least partly within the housing 3 of the device 1. As shown in FIG. 3, the dosing assembly 15 may comprise inclined surface portions 15A formed at least in parts of the dosing assembly 15. The dosing assembly 15 comprises a button 4 (see FIGS. 1A and 1B). The button 4 is displaced with respect to the housing 3 for setting and dispensing a dose. The dosing assembly 15 comprises a drive member 13. The drive member 13 may be a drive sleeve. The dosing assembly 15 comprises a piston rod 11. The drive member 13 is rotatable with respect to the housing 3 for setting a dose. The drive member 13 is rotatable with respect to the housing 3 for delivering the set dose. Movement of the drive member 13 for dispensing the dose is transferred to the piston rod 11 for driving the bung 10 in the distal direction by mechanical cooperation of the drive member 13 and the piston rod 11. The piston rod 11 comprises a thread 12. The thread 12 is arranged on an outer surface of the piston rod 11, as shown in FIG. 2.

The dosing assembly 15 comprises a spring 19. The spring 19 may be a helical coil spring, for example. The spring 19 exerts an axially, in particular distally, directed force onto components of the device 1, which is explained in detail in connection with FIGS. 3 and 4.

The drug delivery device 1 may be a pen-type device, in particular a pen-type injector. The device 1 may be configured for dispensing fixed doses of the drug 7, i.e. doses which may not be varied by a user, or user-settable doses of the drug 7. The device 1 is a re-usable device, which means that the cartridge 2 can be replaced, in particular during a reset operation, by a replacement cartridge for dispensing a plurality of doses from the replacement cartridge.

FIG. 3 schematically shows a perspective side view of parts of the drug delivery device of FIG. 2.

The device 1 further comprises an engagement member 18. The engagement member 18 comprises a circular shape. The engagement member 18 comprises a central opening. The engagement member 18 comprises a nut, for example.

The engagement member 18 is provided around the piston rod 11. In particular, the piston rod 11 is guided through the central opening of the engagement member 18. The engagement member 18 is in, preferably permanent, threaded engagement with the housing 3. The engagement member 18 is in, preferably permanent, threaded engagement with the piston rod 11.

The engagement member 18 comprises interaction elements 18A, 18B. One interaction element 18A is arranged on an inner surface of the engagement member 18. The further interaction element 18B is arranged on an outer surface of the engagement member 18. The respective interaction element 18A, 18B comprises according to this embodiment parts of a thread. Alternatively, the respective interaction element 18A, 18B may comprise a complete thread, in particular a helical thread. Alternatively, the respective interaction element 18A, 18B may comprise one, two, or more projections such as knobs.

The interaction element 18A which is arranged on the inner surface of the engagement member 18 mechanically cooperates with the thread 12 of the piston rod 11 for establishing the threaded engagement between the engagement member 18 and the piston rod 11. In an alternative embodiment (not explicitly shown), the engagement member 18 may comprise the complete thread on the inner surface and the piston rod 11 may comprise parts of a thread or knobs on the outer surface for establishing the threaded engagement between the piston rod 11 and the engagement member 18.

Figure 4:
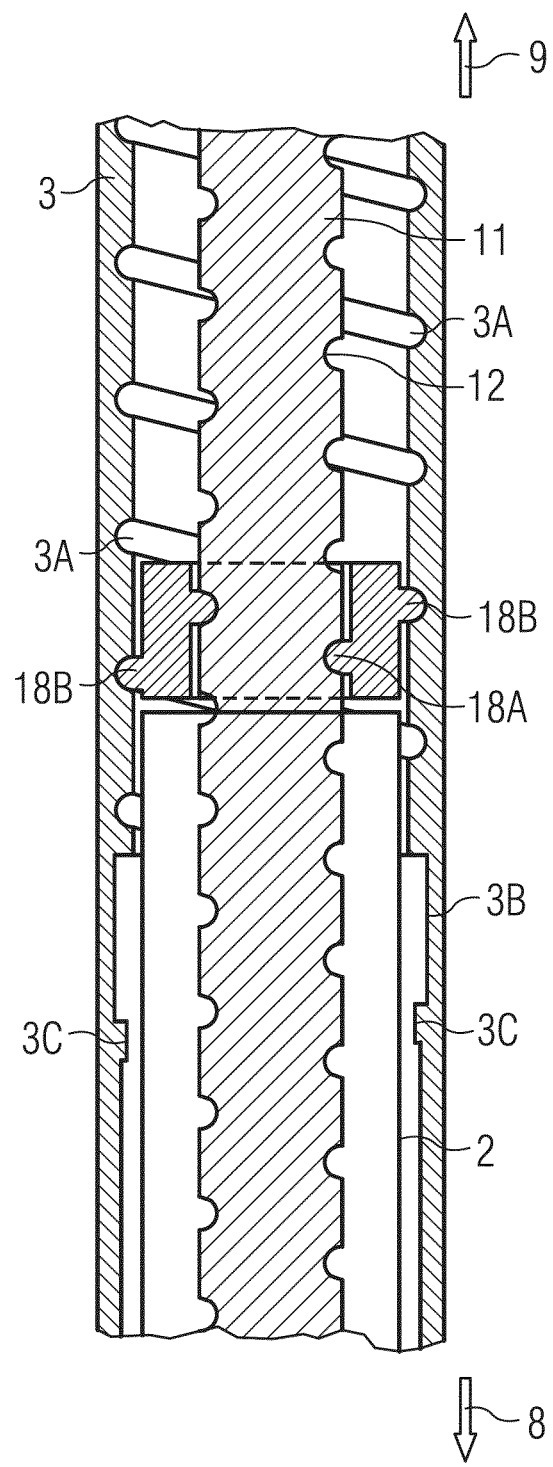

The interaction element 18B which is arranged on the outer surface of the engagement member 18 mechanically cooperates with the housing 3, in particular with a thread 3A of the housing 3 for establishing the threaded engagement between the housing 3 and the engagement member 18. The thread 3A of the housing 3 is provided on an inner surface of the housing 3, as shown in FIG. 4. The thread 3A comprises an indentation on the inner surface of the housing 3. The thread 3A of the housing 3 comprises an end section 3B, in particular a distal end section, which extends circumferentially around the inner surface of the housing 3 (see FIG. 4). In an alternative embodiment (not explicitly shown), the engagement member 18 may comprise the complete thread on its outer surface and the housing 3 may comprise parts of a thread or knobs on the inner surface for establishing the threaded engagement between the housing and the engagement member 18.

The thread 3A on the housing 3 is equally handed as compared to the thread 12 of the piston rod 11. The thread 3A on the housing 3 comprises an equal lead as compared to the thread 12 of the piston rod 11. The thread 3A on the housing 3 comprises an equal pitch as compared to the thread 12 of the piston rod 11. The thread 3A on the housing 3 and the thread 12 of the piston rod 11 are both non-self locking threads.

The engagement member 18 is moveable with respect to the housing 3 and with respect to the piston rod 11 between an operating position and a reset position. In particular, the engagement member 18 is rotated and simultaneously axially displaced during movement of the engagement member 18 between the operating position and the reset position. The simultaneous axial and rotational movement of the engagement member 18 is enabled by the specific shape and structure of the threads on the housing 3 and on the piston rod 11 as described above.

The operating position of the engagement member 18 is arranged more proximally with respect to the housing 3 than the reset position. When the engagement member 18 is in the operating position, the engagement member 18 is secured against axial, in particular distal, movement with respect to the housing 3 and with respect to the piston rod 11 due to mechanical cooperation of the engagement member 18 and the cartridge 2 (see, for example, FIG. 4). In the operation position, the engagement member 18 is biased in the distal direction due to the distally directed force provided by the spring 19. This may help to prevent proximal movement of the engagement member 18 with respect to the housing 3 when the engagement member 18 is in the operating position.

Furthermore, when the engagement member 18 is in the operating position, the engagement member 18 is secured against rotation with respect to the housing 3 and with respect to the piston rod 11. For this purpose, the engagement member 18 comprises teeth 18C. The teeth 18C are arranged on the outer surface of the engagement member 18, for example. Preferably the teeth 18C are arranged in the proximal end section of the engagement member 18. Mechanical cooperation of the teeth 18C with corresponding locking members (not explicitly shown in the Figures) of the housing 3 prevents rotation of the engagement member 18 when the engagement member 18 is in the operation position. Mechanical cooperation of the teeth 18C with the corresponding locking members of the housing 3 may be such that movement of the engagement member 18 with respect to the housing 3 and with respect to the piston rod 11 between the operating position and the reset position is enabled. In particular, the locking connection of the housing 3 and the engagement member 18 by means of mechanical cooperation of the teeth 18C with the corresponding locking members is a releasable connection. In an alternative embodiment (see, for example, FIG. 4), the teeth 18C may be redundant. In this case, rotation of the engagement member 18 with respect to the housing 3 and with respect to the piston rod 11 may be prevented by means of frictional forces, for example.

When the engagement member 18 is in the operating position, the interaction member 18A mechanically cooperates with the thread 12 of the piston rod 11 such that the piston rod 11 is distally displaceable and rotatable in a dose delivery direction for dispensing the dose.

For moving the engagement member 18 from the operating position into the reset position, the cartridge 2 is removed from the device 1. Now, the engagement member 18 is no longer held in its axial position by mechanical cooperation of the cartridge 2 and the engagement member 18 such that the spring 19 drives the engagement member 18 in the distal direction with respect to the housing 3 and with respect to the piston rod 11. Thereby, the teeth 18C are brought out of mechanical cooperation with the blocking members of the housing 3 such that the engagement member 18 is rotatable with respect to the housing 3 due to mechanical cooperation of the interaction element 18B with the thread 3A on the housing 3 and the thread 12 of the piston rod 11. Thereby, the engagement member 18 is also rotated with respect to the piston rod 11 by mechanical cooperation of the interaction elements 18A, with the thread 12 of the piston rod 11 and the thread on the housing 3. This is enabled by the equal lead and hands of the thread on the housing 3 and the thread 12 of the piston rod 11. The engagement member 18 is rotated in the same direction as compared to the rotation direction of the piston rod 11 when the piston rod 11 is axially displaced for dispensing the dose, i.e. the delivery direction as seen from the distal end of the device 1.

The engagement member 18 is rotated and moved distally until the interaction member 18B mechanically cooperates with the circumferential end section 3B of the thread 3A of the housing 3. When the engagement member 18 mechanically cooperates with the circumferential end section 3B, it is freely, in particular bi-directionally, rotatable but no longer distally displaceable with respect to the housing 3. The circumferential end section 3B may comprise a protrusion 3C protruding radially inwardly with respect to the housing 3. The protrusion 3C is arranged in a distal end section of the circumferential end section 3B. The protrusion 3C mechanically cooperates with a distal end section of the engagement member 18 preventing further distal movement of the engagement member 18 with respect to the housing 3 when the engagement member 18 is arranged in the reset position. Accordingly, the distal end section 3B of the thread of the housing 3 forms a distal end stop for the engagement member 18. When the engagement member 18 mechanically cooperates with the circumferential end section 3B, it is in the reset position.

Now, the user can move the piston rod 11 in the proximal direction for resetting the device 1. Thereby, the piston rod 11 is rotated in a reset direction with respect to the housing 3. The reset direction may be opposite to the direction the piston rod 11 is rotated to when delivering the dose.

When the piston rod 11 is moved in the proximal direction, the engagement member 18 is rotated with respect to the housing 3 and with respect to the piston rod 11 due to mechanical cooperation of the interaction elements 18A, 18B with the thread 3A, 3B on the housing 3 and the thread 12 of the piston rod 11. The engagement member 18 is rotated in the direction opposite to the delivery direction in which the engagement member 18 is rotated when it is moved into the reset position.

When the user has moved piston rod 11 into a proximal end position (not shown in the Figures) with respect to the housing 3 during the reset operation, reset of the piston rod 11 is completed. Now, a replacement cartridge can be releasably connected to the housing 3. During this connection operation, the replacement cartridge and/or the cartridge holder 6, in particular the proximal end section thereof, mechanically cooperates with the engagement member 18 for moving the interaction element 18B out of mechanical cooperation with the circumferential end section 3B of the thread of the housing 3. The engagement member 18 is now moved and rotated in the proximal direction with respect to the housing 3 and with respect to the piston rod 11 due to mechanical cooperation of the interaction elements 18A, 18C with the thread 3A on the housing and the thread 12 of the piston rod 11. The engagement member 18 is moved proximally against the distally directed force provided by the spring 19. The engagement member 18 is rotated in the opposite direction as compared to its rotation direction when it is moved from the operating position to the reset position, i.e. in the direction opposite to the delivery direction. Rotation of the engagement member 18 with respect to the housing 3 and with respect to piston rod 11 is in particular enabled due to the equal lead and hands of the thread 3A on the housing 3 and the thread 12 of the piston rod 11.

When the cartridge 2 has reached its final position with respect to the housing 3, in particular when the cartridge 2 is securely connected to the housing 3, the engagement member 18 is back in the operating position. When the engagement member 18 is in the operating position, it is no longer rotationally moveable with respect to the housing 3 due to mechanical cooperation of the teeth 18C with the locking members of the housing 3 as described above. Now, the device is ready for setting and dispensing a dose from the replacement cartridge.

The invention claimed is:

1. An assembly for a drug delivery device comprising:
   a cartridge adapted and arranged to contain at least one dose of a drug, a bung being slidably arranged within the cartridge,
   a housing comprising a distal end and a proximal end,
   a piston rod adapted and arranged for moving the bung in a distal direction with respect to the housing for dispensing a dose of the drug,
   a drive member adapted and arranged for transferring movement to the piston rod for dispensing the dose, and
   an engagement member configured to mechanically cooperate with the piston rod and with the housing,
   wherein the engagement member is moveable between a reset position, where the engagement member is allowed to rotate with respect to the housing, and an operating position, where the engagement member is rotationally locked with respect to the housing, wherein the assembly is configured such that the engagement member is rotated and simultaneously axially displaced during a movement of the engagement member between the operating position and the reset position,
   wherein the engagement member and the housing are threadedly engaged with one another, wherein at least one of the engagement member and the housing comprises a thread and the other one of the engagement member and the housing comprises an interaction element engaging the thread to establish the threaded engagement, and
   wherein the engagement member and the piston rod are engaged with one another so as to allow the engagement member to rotate relative to the piston rod as the engagement member moves between the operating position and the reset position.

2. The assembly of claim 1, wherein the thread comprises an end section which extends circumferentially wherein, when the engagement member is in the reset position, the interaction element mechanically cooperates with the end section such that the engagement member is rotatable with respect to the housing without being axially displaced with respect to the housing.

3. The assembly of claim 1, wherein the thread is provided on the housing.

4. The assembly according to claim 1, wherein the interaction element comprises at least one of a thread or a part of a thread.

5. The assembly according to claim 1, wherein the engagement member and the piston rod are threadedly engaged with one another, wherein at least one of the engagement member and the piston rod comprises a further thread and the other one of the engagement member and the piston rod comprises a further interaction element engaging the further thread to establish the threaded engagement.

6. The assembly according to claim 5, wherein the further interaction element comprises at least one of a thread or a part of a thread.

7. The assembly according to claim 1, wherein, the engagement member comprises a plurality of teeth, wherein, when the engagement member is in the operating position, the teeth mechanically cooperate with mating teeth of the housing such that the engagement member is rotationally locked with respect to the housing.

8. An assembly for a drug delivery device comprising:
a cartridge adapted and arranged to contain at least one dose of a drug, a bung being slidably arranged within the cartridge,
a housing comprising a distal end and a proximal end,
a piston rod adapted and arranged for moving the bung in a distal direction with respect to the housing for dispensing a dose of the drug,
a drive member adapted and arranged for transferring movement to the piston rod for dispensing the dose, and
an engagement member configured to mechanically cooperate with the piston rod and with the housing,
wherein the engagement member is moveable between a reset position, where the engagement member is allowed to rotate with respect to the housing, and an operating position, where the engagement member is rotationally locked with respect to the housing, wherein the assembly is configured such that the engagement member is rotated and simultaneously axially displaced during a movement of the engagement member between the operating position and the reset position,
wherein the engagement member and the housing are threadedly engaged with one another, wherein at least one of the engagement member and the housing comprises a thread and the other one of the engagement member and the housing comprises an interaction element engaging the further thread to establish the threaded engagement,
wherein the engagement member and the piston rod are threadedly engaged with one another, wherein at least one of the engagement member and the piston rod comprises a further thread and the other one of the engagement member and the piston rod comprises a further interaction element engaging the thread to establish the threaded engagement,
wherein the thread provided by at least one of the housing and the engagement member comprises equal lead and hands as compared to the further thread provided by at least one of the engagement member and the piston rod such that the engagement member is rotatable with respect to the piston rod and with respect to the housing when being moved between the reset position and the operating position.

9. An assembly for a drug delivery device comprising:
a cartridge adapted and arranged to contain at least one dose of a drug, a bung being slidably arranged within the cartridge,
a housing comprising a distal end and a proximal end,
a piston rod adapted and arranged for moving the bung in a distal direction with respect to the housing for dispensing a dose of the drug,
a drive member adapted and arranged for transferring movement to the piston rod for dispensing the dose, and
an engagement member configured to mechanically cooperate with the piston rod and with the housing,
wherein the engagement member is moveable between a reset position, where the engagement member is allowed to rotate with respect to the housing, and an operating position, where the engagement member is rotationally locked with respect to the housing, wherein the assembly is configured such that the engagement member is rotated and simultaneously axially displaced during a movement of the engagement member between the operating position and the reset position,
wherein the engagement member and the housing are threadedly engaged with one another, wherein at least one of the engagement member and the housing comprises a thread and the other one of the engagement member and the housing comprises an interaction element engaging the thread to establish the threaded engagement,
wherein the assembly comprises a dosing assembly which is configured to be releasably coupled to the cartridge, and wherein the assembly comprises a spring which is adapted and arranged to exert an axially directed force onto the engagement member such that, when the cartridge is decoupled from the dosing assembly, the engagement member is moved from the operating position into the reset position.

10. The assembly according to claim 9, wherein, when the dosing assembly is coupled to the cartridge, the engagement member is moved into the operating position by mechanical cooperation of the cartridge or a cartridge holder of the device and the engagement member.

* * * * *